United States Patent
Dong et al.

(10) Patent No.: US 8,586,765 B2
(45) Date of Patent: Nov. 19, 2013

(54) PROCESS FOR THE SYNTHESIS OF 3-AMINO-3-CYCLOBUTHYLMETHYL-2-HYDROXYPROPIONAMIDE OR SALTS THEREOF

(75) Inventors: Shuan Dong, Watchung, NJ (US);
Jeonghan Park, Whippany, NJ (US);
Eugene John Vater, Lyndhurst, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 377 days.

(21) Appl. No.: 12/809,775

(22) PCT Filed: Dec. 17, 2008

(86) PCT No.: PCT/US2008/087228
§ 371 (c)(1),
(2), (4) Date: Oct. 20, 2010

(87) PCT Pub. No.: WO2009/085858
PCT Pub. Date: Jul. 9, 2009

(65) Prior Publication Data
US 2011/0034705 A1  Feb. 10, 2011

Related U.S. Application Data

(60) Provisional application No. 61/008,895, filed on Dec. 21, 2007.

(51) Int. Cl.
| C07C 231/12 | (2006.01) |
| C07C 231/06 | (2006.01) |
| C07C 237/14 | (2006.01) |
| C07D 209/52 | (2006.01) |

(52) U.S. Cl.
USPC .......................................... 548/515; 564/130

(58) Field of Classification Search
None
See application file for complete search history.

(56) References Cited

U.S. PATENT DOCUMENTS

| 6,992,220 B2 * | 1/2006 | Chen et al. ............. 564/189 |
| 7,012,066 B2 | 3/2006 | Saskena et al. |
| 7,244,721 B2 | 7/2007 | Saskena et al. |
| RE43,298 E | 4/2012 | Saskena et al. |

FOREIGN PATENT DOCUMENTS

| WO | 2004/113272 A | 12/2004 |
| WO | 2004/113294 A | 12/2004 |

OTHER PUBLICATIONS

Venkatraman, Srikanth et al., "Discovery of (1R, 5S)-N-[3-amino-1-(cyclobutylmethyl)-2,3-dioxopropyl]-3-[2(s)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide (SCH 503034), a selective, potent, orally bioavailable hepatitis C virus NS3 protease inhibitor," 49(20) J. Med. Chem. 6074 (Oct. 1, 2006).

* cited by examiner

Primary Examiner — Sun Jae Loewe
(74) Attorney, Agent, or Firm — Julie M. Lake; Sheldon O. Heber

(57) ABSTRACT

A process for preparing 3-amino-3-cyclobutylmethyl-2-hydroxypropionamide of the Formula I:

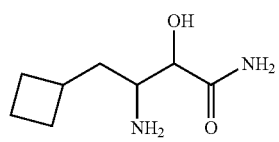

or a salt thereof involves providing a compound of the Formula VI described herein in a solution comprising predominately dimethylsulfoxide (DMSO) and converting this compound directly to the compound of the Formula VIII described herein without working up or isolating the intermediate compound of the Formula VII described herein.

16 Claims, No Drawings

PROCESS FOR THE SYNTHESIS OF 3-AMINO-3-CYCLOBUTHYLMETHYL-2-HYDROXYPROPIONAMIDE OR SALTS THEREOF

This application is the National Stage of International Application No. PCT/US2008/087228 filed on Dec. 17, 2008, which claims the benefit under 35 U.S.C. 119(e) of U.S. Provisional Application No. 61/008,895, filed Dec. 21, 2007, each of which applications are incorporated by reference as if fully set forth herein.

FIELD OF THE INVENTION

This application relates to novel processes for the preparation of 3-amino-3-cyclobutylmethyl-2-hydroxypropionamide or salts thereof.

BACKGROUND OF THE INVENTION

Identification of any publication in this section or any section of this application is not an admission that such publication is prior art to the present invention.

The compound 3-Amino-3-cyclobutylmethyl-2-hydroxypropionamide has the structure of Formula I:

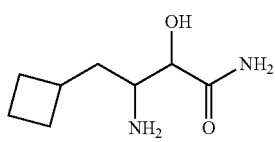

I

The compound of Formula I is a key intermediate used in the preparation of the hepatitis C virus ("HCV") protease inhibitor (1R,2S,5S)-3-azabicyclo[3,1,0]hexane-2-carboxamide, N-[3-amino-1-(cyclobutylmethyl)-2,3-dioxopropyl]-3-[(2S)-2-[[[1,1-dimethylethyl)amino]carbonylamino]-3,3-dimethyl-1-oxobutyl]-6,6-dimethyl having the following structure:

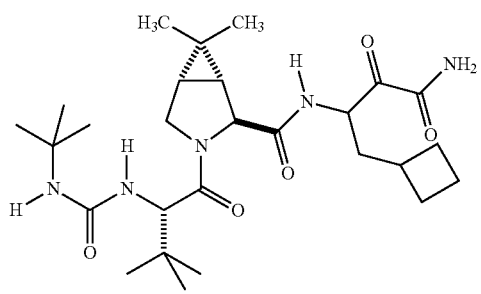

Formula Z

The compound of Formula Z is useful for treating hepatitis C and related disorders. Specifically, the compound of Formula Z is an inhibitor of the HCV NS3/NS4a serine protease.

Processes for preparing, the compound of Formula Z, using the compound of Formula I or salts thereof are described in each of U.S. Pat. No. 7,012,066 and U.S. Pat. No. 7,244,721, the entire contents of which are hereby incorporated fully herein by reference.

U.S. Pat. No. 6,992,220 (hereinafter "the '220 patent") describes a process for preparing the compound of Formula I and salts thereof. The process of making the compound of Formula I and various salts thereof described in the '220 patent is presented in Scheme A, below.

Scheme A

Step (1) alkylating and deprotecting a compound of Formula II to yield a compound of Formula III:

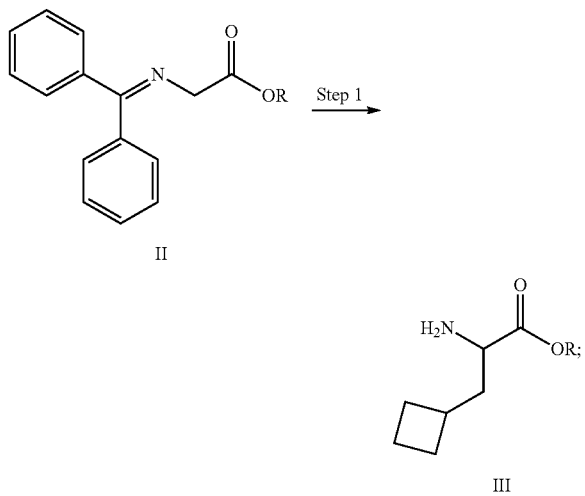

wherein R represents an alkyl group or substituted alkyl group;

Step (2) protecting the compound of Formula III with protecting group (P) to yield a compound of Formula IV:

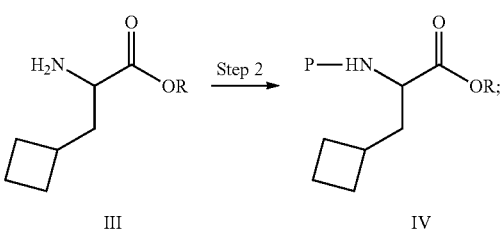

Step (3) reducing the compound of Formula IV to yield a compound of Formula V:

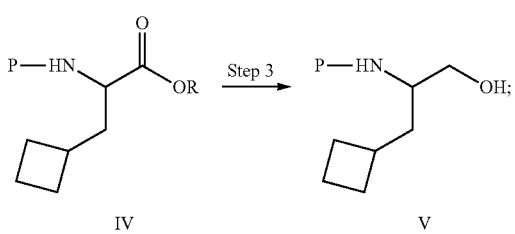

Step (4) oxidizing the compound of Formula V to yield a compound of Formula VI:

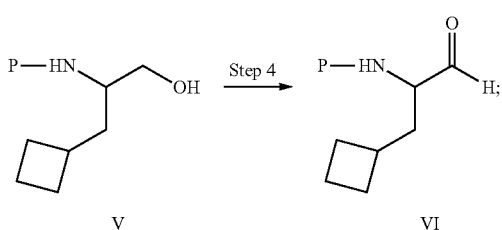

Step (5) reacting the compound of Formula VI with

to yield a compound of Formula VII:

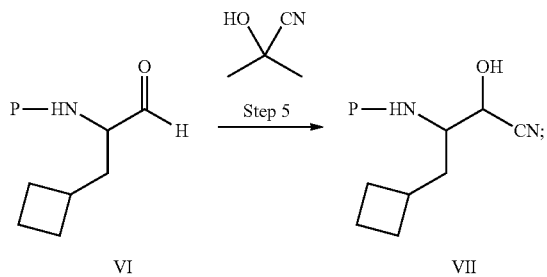

Step (6) hydrating the compound of Formula VII to yield a compound of Formula VIII:

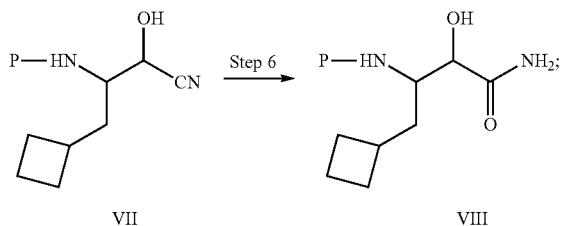

Step (7) deprotecting the compound of Formula VIII to yield the compound of Formula I:

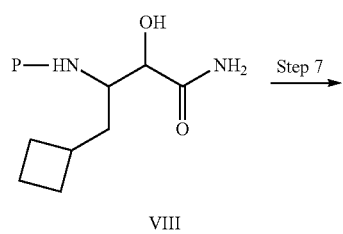

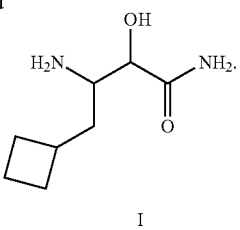

The process described in the '220 patent provides relatively low yields of the product of Formula I from the various intermediates described therein. For example, as described in the example presented in the '220 patent, steps 4 to 7, the process of the '220 patent provides about a 67% solution yield of the compound of the Formula I based on the amount of the compound of Formula V employed, where the protecting group "P" is tert-butoxycarbonyl (Boc).

Moreover, one step of the process of the '220 patent, the step in which the compound of Formula VII is formed, the process of the '220 patent employs metal cyanide, for example, potassium cyanide, which is a toxicity hazard. In addition, in the formation of the compound of Formula VII, the process of the '220 patent includes an aqueous workup step which yields an aqueous cyanide-bearing waste stream. Accordingly, in the example Step 5 of the '220 patent, a tetrabutylammonium iodide phase transfer catalyst is employed along with aqueous potassium cyanide to facilitate reaction between acetone cyanohydrin and the compound of Formula VI dissolved in ethyl acetate. When the reaction between the compound of Formula VI and acetone cyanohydrin is completed, the aqueous layer is separated and the organic layer thus obtained is worked-up by washing with a 20% sodium chloride solution and then concentrated to yield an ethyl acetate layer containing the Boc compound of the Formula VII.

When the process of the '220 patent was scaled to a batch size suitable for the preparation of commercial quantities of the compound of Formula I, a 67.4% of the compound of Formula VIII, based on the amount of the compound of Formula V employed, was obtained. Without wanting to be bound by theory, it is believed a significant portion of the yield losses observed are due to decomposition of the Formula VII during the required aqueous workup at the end of the acetone cyanohydrin reaction. It is also believed that a high impurity profile in the compound of the Formula VIII prepared in accordance with the process of the '220 patent is due to decomposition of the compound of Formula VII during workup, which necessitated multiple slurry steps to obtain a suitably pure product when the process was run on a commercial scale.

OBJECTIVES AND SUMMARY

In view of the foregoing, what is needed is a process for preparing the compound of Formula I which eliminates the need for workers to handle solid, metal cyanide, and in addition minimizes decomposition of the intermediate compound of Formula VII in the reaction mixture during processing. Moreover, what is needed is a process which reduces or eliminates the amount of cyanide-bearing waste generated in the process. Moreover, what is needed is a process which provides the compound of Formula I in higher yields.

These and other needs are met by the process of the present invention which in one aspect is a novel process in accordance with Scheme I below:

Scheme I

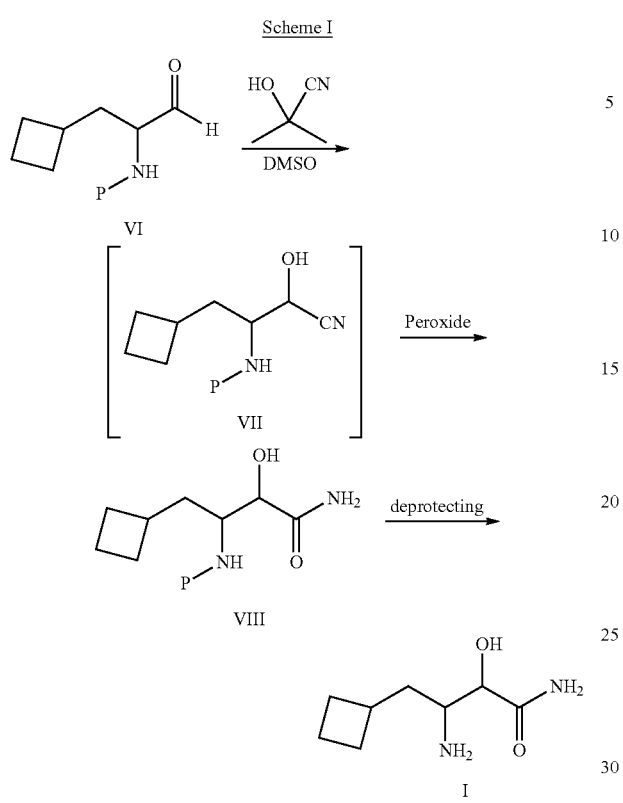

the process comprising:

(i) reacting acetone cyanohydrin with a solution comprising the compound of Formula VI and a solvent which is substantially dimethyl sulfoxide (DMSO), thereby forming the compound of the Formula VII, wherein, "P" is an acid-labile protecting group;

(ii) reacting the reaction mixture obtained from Step "i" with peroxide, thereby forming the compound of Formula VIII in situ; and (iii) reacting the reaction mixture obtained in Step (ii) with an acid, thereby deprotecting the compound of the Formula VIII and yielding the compound of the Formula I.

In some embodiments, preferably P is BOC (tertiarybutyloxycarbonyl, moiety, [(CH$_3$)$_3$C—O—C(O)—] which forms a carbamate acid ester with the amino-nitrogen). In some embodiments, it is preferred to carry out the provision a DMSO solution of the compound of the Formula VI in accordance with the process presented in Scheme II,

Scheme II

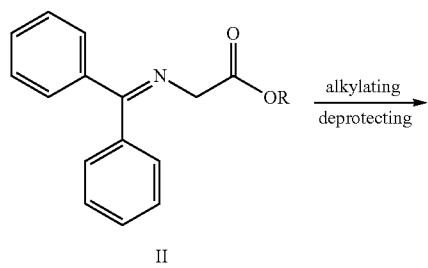

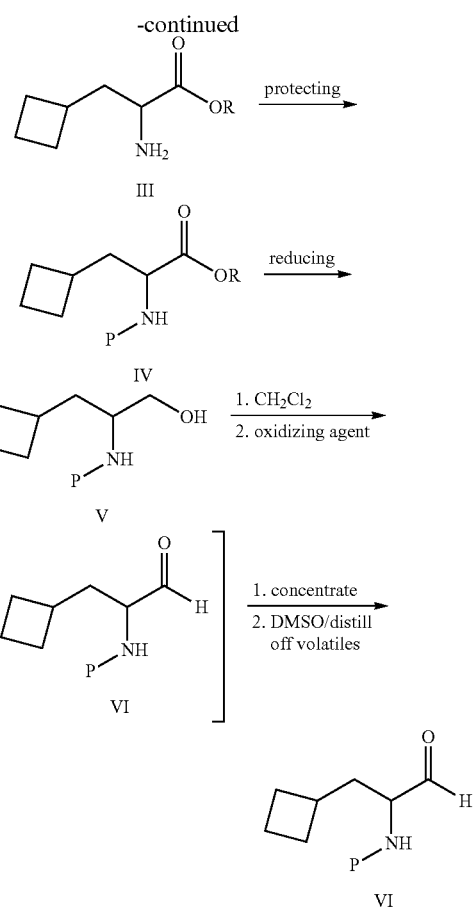

the process comprising:

(i) alkylating the compound of Formula II, where R represents an alkyl group or substituted alkyl group, with a cyclobutylmethylhalide in the presence of a base and deprotecting the product to yield the compound of the Formula III;

(ii) protecting the amino group in the compound of Formula III isolated from Step "i" to provide the compound of Formula IV, wherein P is an acid labile nitrogen protecting group;

(iii) reducing the compound of Formula IV to form the corresponding alcohol of Formula V;

(iv) oxidizing a dichloromethane solution of the compound of the Formula V to yield the compound of the Formula VI; and (v) concentrating the dichloromethane solution from Step "iv" to a minimum volume, mixing DMSO with the concentrate and distilling off volatiles from the mixture.

In some embodiments of the invention, with reference to Scheme II, it is preferred to carry out one or more of the processes describe in Step "i", Step "ii", Step "iii", and/or Step "iv" in accordance with the experimental details described and set forth in the above-mentioned '220 patent, the entire contents of which have already been incorporated herein by reference. In some embodiments it is preferred to adapt the conditions of the TEMPO mediated oxidizing step to those suitable for running the oxidation in dichloromethane, for example, the conditions presented in Example I, below. Details of aspects of the inventive process described herein are set forth below.

Another aspect of the present invention is a novel process for preparing (1R,2S,5S)-3-azabicyclo[3,1,0]hexane-2-carboxamide, N-[3-amino-1-(cyclobutylmethyl)-2,3-dioxopropyl]-3-[(2S)-2-[[[(1,1-dimethylethyl)amino]carbonylamino]-3,3-dimethyl-1-oxobutyl]-6,6-dimethyl of the Formula Z:

Formula Z

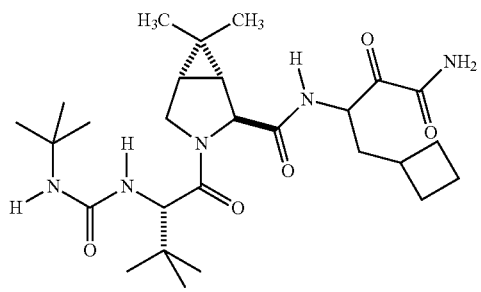

or a salt thereof;
the process comprising:
(i) preparing the compound of the Formula I or a salt thereof according to the inventive process described herein; and
(ii) converting the compound of Formula I or the salt thereof to the compound of the Formula Z by a process described in either U.S. Pat. No. 7,012,066 or U.S. Pat. No. 7,244,721, each of which are incorporated herein by reference.

Other aspects and advantages of the invention will become apparent from the following description of the invention.

DETAILED DESCRIPTION OF THE INVENTION

As mentioned above, the present invention process provides a process for converting the compound of the Formula VI to the compound of the Formula VIII in isolated yields of greater than 80% based on the amount of the compound of Formula V initially employed. This represents an isolated yield from the process of the present invention which exceeds by more than 20% the solution yield (product not isolated) provided by the process described in the U.S. Pat. No. 6,992,220 (the '220 patent), which reported a 67% solution yield based on the amount of the compound of Formula V employed.

The inventors have found that when the process described in the '220 patent is scaled-up to a size suitable for commercial production, impurities in the isolate product arising from the process necessitate the inclusion of interim purifying procedures, for example, multiple slurry steps, to obtain the compound of Formula VIII in a suitably pure form. These multiple purification steps result in yield decrease in the isolated product. Accordingly, the present process provides even greater improvement in the isolated yield of the compound of Formula I than is available from the '220 patent process. Moreover, the present invention process utilizes an acetone cyanohydrin reaction under conditions which eliminates the aqueous workup previously required, thereby improving process efficiency. As mentioned above also, the process of the present invention additionally reduces the amount of aqueous cyanide waste co-generated during the process, thus reducing waste treatment requirements associated with carrying out the process.

With reference to Process Schemes A presented in the Background section above, which describes the process described in U.S. Pat. No. 6,992,220 (the '220 patent), the process of the present invention provides a number of improvements to the steps identified in Scheme A as Steps 4 to 6. These improvements are presented as Steps I and II in Scheme III, below, wherein BOC is a tertiarybutyloxycarbonyl, moiety, [(CH$_3$)$_3$C—O—C(O)—], which forms a carbamate acid ester with the amino-nitrogen).

SCHEME III

Step I

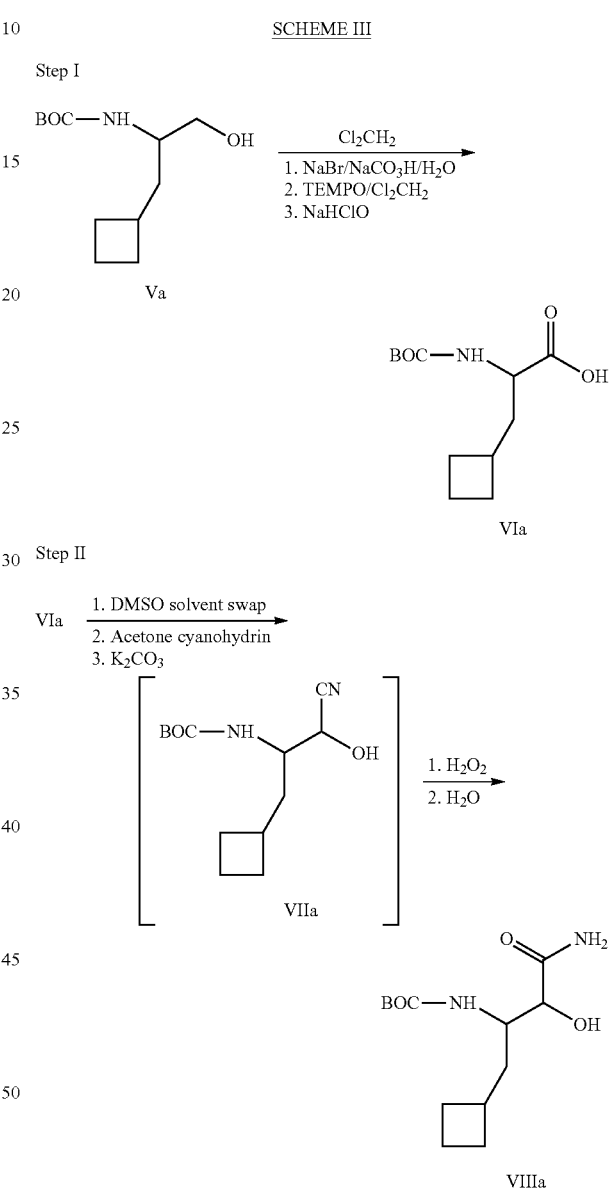

Step II

The process of the present invention utilizes a TEMPO mediated oxidation similar to that described in the '220 patent, however in the present invention process it is adapted to run in a dichloromethane reaction solvent instead of ethyl acetate. Although other solvents can be used, for example, ethyl acetate, it has been surprisingly found that dichloromethane is a suitable solvent for the TEMPO mediated oxidation which provides a clean reaction.

Moreover, it has been found, surprisingly, that the subsequent reaction with acetone cyanohydrin to form the compound of Formula VII from the compound of Formula VI can be run in DMSO using potassium carbonate as a catalyst, thus providing an environment in which the acetone cyanohydrin reaction can be run without a phase transfer catalyst or the use of a metal cyanide compound. Moreover, when the cyanohydrin reaction is run in DMSO, the reaction mixture thus obtained provides a medium in which the product can be oxidized using peroxide without necessitating a further workup or solvent swap. Thus, surprisingly, a cyanohydrin reaction forming a compound of Formula VII from a compound of Formula VI, and an oxidation reaction to oxidize a compound of Formula VII to an amide amino alcohol of Formula VIII can be carried out as a one-pot process, eliminating the need for isolation of the compound of Formula VII, or any additional work-up and/or solvent swapping prior to the oxidation reaction. Accordingly, the present process effectively eliminates a step and a source of decomposition and yield loss which was present in the process described in the '220 patent.

Accordingly, in some embodiments of the invention employing dichloromethane in Step I, when the compound of Formula V employed in Step I is a compound of Formula Va, it is preferred to carry out Step I using an amount of dichloromethane the is from about 5× to about 10× (vol/w) of methylene chloride/the compound of Formula Va, preferably about 6.5× methylene chloride (vol/w). In some embodiments of the invention it is preferred to carry out Step I using from about 0.4 to about 1.0 equivalents of sodium bromide, preferably about 0.5 equivalents of sodium bromide. In some embodiments of the invention it is preferred to carry out Step I using from about 0.8 to about 1.5 equivalents, preferably 1.5 equivalents of sodium bicarbonate. In some embodiments of the invention it is preferred to carry out Step I using from about 0.001× to about 0.01× (w/w) of 2,2,6,6-tetramethyl-1-piperidinyloxy radical relative to the amount of the compound of Formula V employed, preferably the radical is employed in an amount of about 0.0025× (w/w). In some embodiments it is preferred to carry out the oxidation process in Step I using sodium hypochlorite as the oxidizing agent (NaClO). In some embodiments employing sodium hypochlorite it is preferred to employ from about 0.95 equivalents to about 1.2 equivalents of sodium hypochlorite based on the amount of the compound of Formula V employed, preferably about 1.05 equivalents. In some embodiments it is preferred to carry out Step I by initially adding one equivalent of sodium hypochlorite, monitor the reaction for a period of time, preferably about 20 minutes after addition of the hypochlorite, and add an additional amount of sodium hypochlorite based on the amount of unreacted alcohol present in the reaction mixture. In some embodiments it is preferred to quench the excess hypochlorite used in the reaction by contacting the reaction mixture with an aqueous solution of sodium thiosulfate, preferably a solution made using 13 g of sodium thiosulfate in each 100 ml of water.

In some embodiments of the present invention it is preferred to carry out Step I at a temperature of from about $(-10)°$ C. to about $(+10)°$ C., preferably at a temperature of from about $(-5)°$ C. to about $(0)°$ C.

Although dichlormethane is preferred as a solvent form carrying out Step I, it will be appreciated that other low polarity, non-protic, low boiling solvents may be alternatively employed. It will be appreciated also that oxidizing agents other than sodium hypochlorite which are compatible with the solvent system selected may be used without departing from the invention.

It will also be appreciated that the compound of Formula VIa can be prepared in any manner, isolated, and taken up in DMSO to carry out Step II of Scheme III without departing from the scope of the invention.

In some embodiments of the invention it is preferred to concentrate the dichloromethane solution of the compound of Formula VI prepared in accordance with Step I of Scheme III prior to performing a "solvent swap" to DMSO, the reaction solvent in which Step II of Scheme III is carried out. In some embodiments it is preferred to concentrate the solution by applying a vacuum of from about 60 torr to about 80 torr and maintaining the temperature of the solution below about 25° C. until solvent distilled ceases. Although it will be appreciated that other means of concentrating the solution may be employed without departing from the scope of the present invention. In some embodiments of the invention, after the dichloromethane solution has been concentrated it is preferred to perform a "solvent swap" by adding DMSO and again distilling off volatiles by applying a vacuum of from about 60 torr to about 80 torr and maintaining the temperature of the solution below about 25° C. until solvent distilled again ceases. In some embodiments it is preferred to add an amount of DMSO that is from about 1× vol/w, (based on the weight of the compound of Formula VI present in the dichloromethane concentrate) to about 10× vol/w, preferably from about 2× vol/w to about 4× vol/w.

In accordance with the present invention, in Step 2 of the process the compound of Formula VI is reacted with acetone cyanohydrin in DMSO catalyzed by the addition of an aliquot of potassium carbonate, which permits direct reaction between the cyanohydrin and the compound of Formula VI, forming the intermediate compound of Formula VII, without the need for a phase transfer catalyst or a metal cyanide present. The use of DMSO as a reaction solvent at this stage also permits subsequent oxidation of the compound of Formula VII to the compound of Formula VIII to be carried out without an additional solvent swap, workup, or isolation of the intermediate compound and thus reduces decomposition of the compound of Formula VII.

Moreover, by using the reaction mixture directly in the subsequent oxidation step, any cyanide waste generated during the cyanohydrin reaction is decomposed in situ during subsequent treatment of the reaction mixture with peroxide. Thus, no separate cyanide-containing waste stream is generated during the reaction which must subsequently be treated.

With reference to Step II of Scheme III, in some embodiments of the present invention it is preferred to perform the "solvent swap" to DMSO, as described above, and subsequently add an amount of acetone cyanohydrin is added to the DMSO solution containing Compound VI in an amount of from about 0.1× w/w (relative to the amount of Compound VI in the solution) to about 1.0× w/w, preferably from about 0.3× w/w to about 0.5× w/w relative to the amount of the compound of Formula VI in reaction mixture. In some embodiments it is preferred to add and aliquot of potassium carbonate to the reaction mixture after addition of the cyanohydrin to catalyze the reaction between the compound of Formula VIa and acetone cyanohydrin. In some embodiments it is preferred to add potassium carbonate catalyst in an amount up to about 0.1× w/w relative to the amount of compound of Formula VI in the reaction mixture, more preferably potassium carbonate is added in an amount that is from about 0.01× w/w to about 0.03× w/w relative to the amount of the compound of Formula VI in the reaction mixture.

In some embodiments of the present invention it is preferred to monitor the reaction by HPLC and carry out the peroxide reaction when HPLC results indicate that conversion of the compound of Formula VI has been completely consumed. Accordingly, in some embodiments, when the compound of Formula VI is consumed in the reaction mixture, it is preferred to add to the reaction mixture a second aliquot of potassium carbonate to neutralize the reaction mixture in preparation to carry out the oxidation reaction. In most applications the neutralization will require a second aliquot of potassium carbonate after the compound of Formula VI has been consumed in an amount of from about 0.1× w/w to about 1.0× w/w relative to the amount of the compound of Formula VII present in solution, more preferably the second aliquot of potassium carbonate is added in an amount of from about 0.3× w/w to about 0.5× w/w relative to the amount of the compound of Formula VII in solution. In some embodiments of the reaction, once the reaction is neutralized by the addition of a second aliquot of potassium carbonate, it is preferred to heat the reaction mixture above ambient, preferably to a temperature of from about 35° C. to about 45° C., more preferably to about 40° C., and add hydrogen peroxide aqueous solution to effect oxidation of the compound of Formula VII to the compound of Formula VIII after the reaction mixture is at temperature. In some embodiments it is preferred to react the mixture with hydrogen peroxide for a period of about 4 hours while maintaining the reaction mixture at a temperature of from about 35° C. to about 45° C.

In some embodiments it is preferred to add an amount of hydrogen peroxide of from about 0.5× to about 3× w/w relative to the amount of Compound VII in the reaction mixture, preferably from about 0.7× w/w to about 0.9× w/w relative to the amount of Compound VII in the reaction mixture. Although it is not believed that the concentration of hydrogen peroxide used in the phase of Step II of Scheme III is critical, in some embodiments it is preferred to employ a concentration of hydrogen peroxide providing a 35% strength hydrogen peroxide solution.

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, cyano, hydroxy, alkoxy, alkylthio, amino, —NH(alkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, and trifluoromethyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

The term "optionally substituted" means optional substitution with the specified groups, radicals or moieties.

Certain compounds in Schemes 1 and 2 may be protected on a nitrogen atom with a protecting group P. Preferably, in the improved process steps of the invention, the protecting group employed is a tertiarybutyloxycarbonyl moiety, [(CH$_3$)$_3$C—O—C(O)—] which forms a carbamate acid ester with the amino-nitrogen), although it will be appreciated that other suitable groups can be employed and remain within the scope of the invention. Examples of acid labile N-protecting groups which can be employed to carry out the invention include, but are not limited to, allyl, methoxymethyl, benzyloxymethyl, CY$_3$CO (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("Boc" also referred to as "t-Boc" by some chemists), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate and S-benzylcarbamate. Preferred N-protecting groups include methylcarbamate, 2-trimethylsilylethyl carbamate, 1-methyl-1-phenylethyl carbamate, t-butyl carbamate ("Boc"), cyclobutyl carbamate, 1-methylcyclobutyl carbamate, adamantyl carbamate, vinyl carbamate, allyl carbamate, cinnamyl carbamate, 8-quinolyl carbamate, benzyl carbamate, 9-anthrylmethyl carbamate, diphenylmethyl carbamate, S-benzylcarbamate, more preferably Boc.

As noted above, basic process conditions, especially for the steps in Scheme II leading up to the production of Compound VI in dichloromethane (CH$_2$Cl$_2$) can be found in the '220 patent. It will be appreciated, however, that any means can be used to provide the compound of Formula VI, preferably the compound of Formula VIa, and still be within the scope of the present invention.

In some preferred embodiments, Compound V is oxidized to Compound VI by subjecting Compound V to an oxidizing agent in a suitable solvent. In a preferred embodiment, the solvent is ethyl acetate or tert-butyl methyl ether or, especially, dichloromethane. Where the solvent is dichloromethane, it is used in an amount of 5 to 10 times the amount of Compound V, preferably 6-7 times the amount of Compound V.

The oxidizing agent can be any suitable oxidizing agent, but is preferably sodium hypochlorite. Where sodium hypochlorite is employed, it is employed in an amount of 0.95 to 1.2 molar equivalents, preferably 1.00 to 1.05 molar equivalents.

The oxidation is preferably carried out in the presence of one or more catalysts and a base. Especially preferred catalysts include 2,2,6,6-tetramethyl-1-piperidinyloxy (TEMPO), which is employed in an amount of 0.001 to 0.01 times the amount of Compound V in the reaction mixture, preferably 0.0025 times the amount of Compound V in the reaction mixture; and metal bromide, especially, sodium bromide, which is employed in an amount of 0.4 to 1.0 molar equivalents, preferably about 0.5 molar equivalents. The base is especially sodium bicarbonate or the like, which is preferably employed in an amount of 0.8 to 1.5 molar equivalents, especially about 1.5 molar equivalents.

The reaction temperature for the oxidation ranges from −10° C. to +10° C., preferably from −5° C. to 0° C.

Exemplary embodiments of the present invention will now be described in greater detail with reference to the following non-limiting examples.

EXAMPLES

Unless otherwise stated, the following abbreviations have the stated meanings in the Examples below:

MHz=Megahertz
NMR=nuclear magnetic resonance spectroscopy
mL=milliliters
g=grams
THF=tetrahydrofuran
TFA=trifluoroacetic acid
TEMPO=2,2,6,6-Tetramethyl-1-piperidinyloxy radical
DMSO=dimethylsulfoxide
TBME=t-butylmethyl ether
t-Boc=t-butoxycarbonate Example I TEMPO Mediated Oxidation of Compound Va to Compound VIa in Dichloromethane

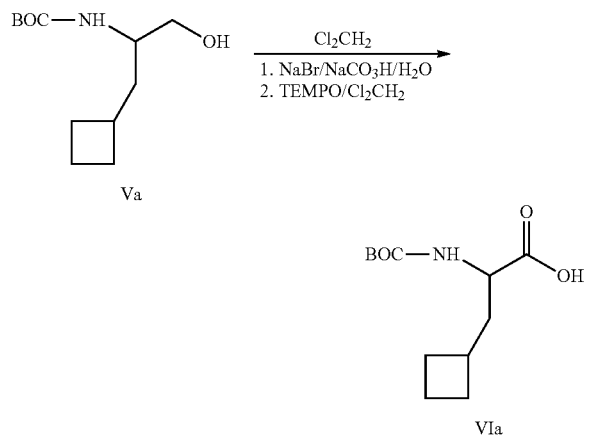

To a solution made from 100 g of 2-t-butoxycarbonylamino-3-cyclobutyl-1-propanol (the compound of Formula Va, provided in accordance with the procedures described in U.S. Pat. No. 6,992,220) dissolved in 650 mL of dichloromethane, which was cooled to (−4)° C., was added a slurry made adding 22.5 g of sodium bromide (0.5 equivalent) and 55 g of sodium bicarbonate (1.5 equivalent) to 80 ml water. To the resulting mixture was added a solution made by dissolving 0.25 g of 2,2,6,6-Tetramethyl-1-piperidinyloxy, free radical (TEMPO reagent) in 3 mL of dichloromethane. The reaction mixture was cooled to (−4)° C., and stirred for 10 minutes. At the end of the stirring period, 525 mL of a 5.5 wt. % aqueous sodium hypochlorite was added over a 1.5 hour period (hypochlorite activity titrated to be 1.0 equivalent) while maintaining the reaction mixture temperature between (−5)° C. and 0° C. The mixture was then stirred for about 20 minutes while being monitored by liquid chromatography for the residual amount of starting alcohol. At the end of 20 minutes an additional amount of sodium hypochlorite equivalent to the amount of unreacted starting alcohol detected was charged over a 20 minute period while maintaining the temperature of the reaction mixture between (−4)° C. and 0° C. The reaction mixture was then stirred for 10 minutes. At the end of the stirring period excess hypochlorite was quenched by adding a solution of 13 g of sodium thiosulfate in 100 ml water over about 5 minutes while allowing the reaction mixture to warm to 15° C. The mixture was stirred for 30 minutes while adding an additional 400 ml of water to completely dissolve the inorganic salts present. Agitation was stopped and the reaction mixture allowed to settle, whereupon the phases were split. The organic phase, containing the product was washed with 150 mL of saturated brine for 10 minutes and then the layers were split then separated. The organic layer was dried by treatment with anhydrous magnesium sulfate and filtration. The dichloromethane solution contained Compound VIa (active 90.6 g; 91.4% molar yield): $^1$H NMR (400 MHz, CD$_3$Cl$_3$) δ 1.42 (9H, s), 1.70 (4H, m), 1.90 (2H, m), 2.10 (2H, m), 2.45 (1H, m), 4.20 (1H, m), 5.00 (1H, s), 9.60 (1H, s).

Example II

One Pot Synthesis of Compound VIIIa from Compound VIa Using DMSO Reaction Media

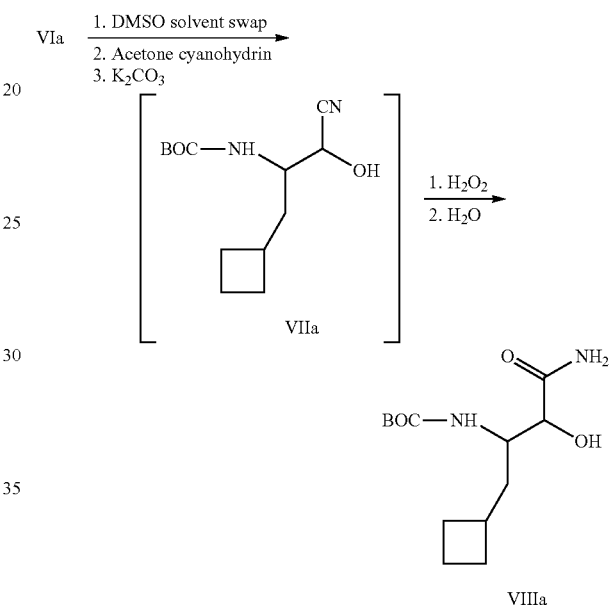

An amount of a methylene chloride solution of the Compound VIa prepared in Example I which was found by HPLC to contain 17.44 g of the compound of Formula VIa in methylene chloride prepared in the previous example was concentrated under vacuum (60-80 torr) to a minimum volume while maintaining a batch temperature below 25° C. (concentration was discontinued when distillation at 25° C. ceased). When distillation had stopped, to the concentrate was added 59 mL of DMSO. The mixture was concentrated again under the same condition (60-80 torr, maintaining the reaction mixture below 25° C.) until no methylene chloride was detected in the mixture by NMR. To the reaction mixture (the solvent of which substantially comprised. DMSO) was added 7.8 mL of acetone cyanohydrin (Aldrich, used as received) followed by 0.3 g of potassium carbonate. The reaction mixture is agitated at room temperature for 16 hours until no starting Compound VIa was detectable by HPLC. The slurry was further charged with 8.0 g of potassium carbonate and heated to 40° C., followed by addition of 14.5 mL of hydrogen peroxide (35%) over 4 hours while maintaining a batch temperature between 35° C. and 45° C. After stirring the reaction mixture at 40° C. for an additional 1 hr, 183 mL of water was added slowly while maintaining the temperature of the reaction mixture at 40° C. Following addition of the water, the mixture was stirred for 1 hour additional. The resulting slurry was cooled to 0° C. and agitated for 6 hours while maintaining the mixture at 0° C. The product was isolated by filtration followed by washing with four 20 mL aliquots of water. The product was dried in vacuum oven at 60° C. for 12 h to afford a white solid (18.75 g, 89.7% yield): $^1$H NMR (400 MHz, CDCl$_3$) δ 1.40 (9H, m), 1.70 (4H, m), 1.85 (2H, m), 1.90 (2H, m), 2.15 (1H, m), 3.50 (1H, m), 3.80-4.00 (1H, m), 4.60 (1H, m), 5.20 (1H, s), 6.50 (1H, m).

The above description of the invention is intended to be illustrative and not limiting. Various changes or modifications in the embodiments described herein may occur to those skilled in the art. These changes can be made without departing from the scope or spirit of the invention.

What is claimed is:

1. A process for preparing 3-amino-3-cyclobutylmethyl-2-hydroxypropionamide of the Formula I:

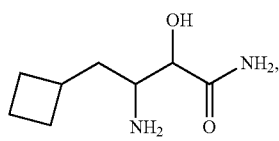

Formula I said process comprising:
(i) reacting acetone cyanohydrin with a solution comprising a compound of Formula VI,

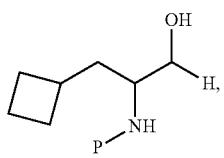

Formula VI and a solvent which is substantially dimethyl sulfoxide (DMSO), thereby forming a compound of Formula VII,

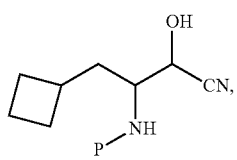

Formula VII wherein, "P" is an acid-labile protecting group and wherein the reaction is catalyzed by up to 0.1× w/w of potassium carbonate;
(ii) reacting the reaction mixture obtained from Step (i) with peroxide, thereby forming in situ a compound of Formula VIII,

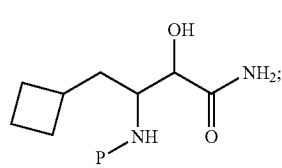

Formula VIII and
(iii) reacting the reaction mixture obtained in Step (ii) with an acid, thereby deprotecting the compound of Formula VIII and yielding the compound of the Formula I.

2. The process of claim 1 wherein acetone cyanohydrin is added in an amount of from about 0.1× w/w to about 1.0 w/w relative to the amount of compound of Formula VI present in the reaction mixture.

3. The process of claim 2 wherein the cyanohydrin reaction is run at room temperature.

4. The process of claim 2 wherein, prior to the peroxide reaction Step (ii), the reaction mixture is neutralized with an aliquot of potassium carbonate of from about 0.1× w/w to about 1.0× w/w relative to the amount of the compound of Formula VII present in the reaction mixture.

5. The process of claim 2 wherein, the source of the peroxide used in Step (ii) is a 35% aqueous hydrogen peroxide solution which is added in an amount to provide from about 0.5× w/w to about 3.0× w/w relative to the amount of the compound of Formula VII present in the reaction mixture.

6. The process of claim 5 wherein the reaction step (ii) is run at a temperature of from about 35° C. to about 45° C.

7. The process according to claim 1, wherein the solution employed in Step (i) is provided by a process that comprises:
a) reacting a dichloromethane solution of the compound of the Formula V,

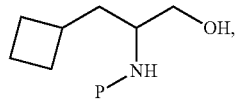

Formula V with an oxidizing agent to yield the compound of the Formula VI,

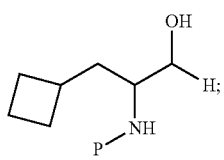

Formula VI and
b) concentrating said dichloromethane solution of the compound of Formula VI prepared in Step a) by distilling off volatiles at a temperature of about 25° C. or less and a pressure of from about 60 torr to about 80 torr.

8. The process of claim 7, wherein the oxidation reaction Step a) is run using 2,2,6,6-tetramethyl-1-piperidinyloxy radical (TEMPO) mediated sodium hypochlorite as the oxidizing agent.

9. The process according to claim 8, wherein the TEMPO is employed in an amount ranging from about 0.001× w/w to about 0.01× w/w relative to the amount of the compound of Formula V present in the reaction mixture.

10. The process according to claim 9, wherein the TEMPO is employed in an amount of about 0.0025 times the amount of compound of Formula V.

11. The process according to claim 8, wherein the oxidizing agent is employed in an amount of 0.95 to 1.2 molar equivalents.

12. The process according to claim 11, wherein the oxidizing agent is employed in an amount of 1.00 to 1.05 molar equivalents.

13. The process according to claim 11, wherein the oxidizing is conducted at a temperature of from −10° C. to +10° C.

14. The process according to claim 13, wherein the oxidizing is conducted at a temperature of from −5° C. to 0° C.

15. The process according to claim 7, wherein the compound of Formula V is provided by a process that comprising:
(i) alkylating the compound of Formula II,

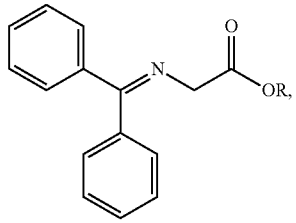

Formula II wherein R represents an alkyl group or substituted alkyl group, by reaction with a cyclobutylmethylhalide in the presence of a base and deprotecting the product to yield the compound of the Formula III,

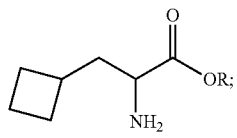

Formula III (ii) protecting the amino group in the compound of Formula III isolated from Step (i) to provide the compound of Formula IV,

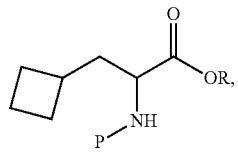

Formula IV wherein P is an acid-labile nitrogen protecting group; and (iii) reducing the compound of Formula IV obtained in Step (ii) to form the corresponding alcohol of Formula V.

16. The process of claim 15, wherein: "R" is ethyl-; Step (i) carried out by alkylating the compound of Formula II with bromomethylcyclobutane in the presence of potassium tertiary butoxide then the reaction mixture is worked up with HCl followed by aqueous potassium carbonate and the resulting compound of Formula III, wherein "R" is ethyl, is extracted into tertiary butyl methyl ether; Step (ii) is carried out by treating the MTBE solution of the Compound of Formula III with ditertiarybutyldicarbonate, yielding the compound of Formula IV, wherein "P" is a tertiarybutoxycarbonyl protecting group; and wherein Step (iii) is carried out by treating the worked-up reaction mixture from Step (ii) with lithium borohydride and crystallizing the product alcohol of Formula V, wherein "P" is a butoxycarbonyl protecting group.

* * * * *

UNITED STATES PATENT AND TRADEMARK OFFICE
CERTIFICATE OF CORRECTION

PATENT NO. : 8,586,765 B2
APPLICATION NO. : 12/809775
DATED : November 19, 2013
INVENTOR(S) : Dong et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 567 days.

Signed and Sealed this
Twenty-second Day of September, 2015

Michelle K. Lee
*Director of the United States Patent and Trademark Office*